United States Patent [19]
Buttram et al.

[11] Patent Number: 5,648,471
[45] Date of Patent: Jul. 15, 1997

[54] ONE VIAL METHOD FOR LABELING ANTIBODIES WITH TECHNETIUM-99M

[75] Inventors: Scott Buttram; Richard T. Dean, both of Downingtown; John Lister-James, Glenmoore; Koon Yan Pak, Norristown, all of Pa.

[73] Assignee: Centocor, Inc., Malvern, Pa.

[21] Appl. No.: 666,421

[22] Filed: Mar. 7, 1991

Related U.S. Application Data

[63] Continuation of Ser. No. 128,328, Dec. 3, 1987, abandoned.

[51] Int. Cl.$^6$ .......................... A61K 51/10; C07K 16/00
[52] U.S. Cl. .......................... 424/1.9; 530/391.5
[58] Field of Search .......................... 424/1.1, 85.8, 424/1.49, 1.53, 179.1; 436/512, 547, 804; 514/492; 530/388, 390, 400, 391.3, 391.5, 391.7, 391.9

[56] References Cited

U.S. PATENT DOCUMENTS

| | | | |
|---|---|---|---|
| 4,113,850 | 9/1978 | Benes | 424/1.65 |
| 4,305,922 | 12/1981 | Rhodes | 530/363 |
| 4,421,735 | 12/1983 | Haber et al. | 424/1.45 |
| 4,424,200 | 1/1984 | Crockford et al. | 424/1.49 |
| 4,454,106 | 6/1984 | Gansow et al. | 424/1.53 |
| 4,472,509 | 9/1984 | Gansow et al. | 436/548 |
| 4,478,815 | 10/1984 | Burchiel et al. | 424/1.49 |
| 4,652,440 | 3/1987 | Paik et al. | 424/1.49 |

(List continued on next page.)

FOREIGN PATENT DOCUMENTS

| | | |
|---|---|---|
| 0083129 | 7/1983 | European Pat. Off. . |
| 0173629 | 3/1986 | European Pat. Off. . |
| 0178125 | 4/1986 | European Pat. Off. . |
| 0188256 | 7/1986 | European Pat. Off. . |
| 0237150 | 9/1987 | European Pat. Off. . |
| 2109407 | 6/1983 | United Kingdom . |

OTHER PUBLICATIONS

Khaw et al., "Myocardial Infarction Imaging of Antibodies to Canine Myosin with Indium–111–Diethylenetriamine Pentaacetic Acid," *Science* 209:295–297 (1980).

Krejcarek and Tucker, "Covalent Attachment of Chelating Groups to Macromolecules," *Biochem. Biophys. Res. Commun.*, 77:581–585 (1977).

Childs an Hnatowich, "Optimum Conditions for Labeling of DTPA–Coupled Antibodies with Technetium–99m," *J. Nucl. Med.*, 26:293–299 (1985).

PCT Patent Application PCT/AU87/04164, I. McKenzie et al., "Technetium–Antibody Conjugate," Jul. 16, 1987.

Fritzberg et al., "Radiopharmaceutical chemistry V: Antibodies", *J. Nucl. Med.*, 27:957–958 (1986).

Khaw et al., "Technium–99m Labeling of Antibodies to Cardiac Myosin Fab and to Human Fibrinogen," *The Journal of Nuclear Medicine*, 23 (11): 1011–1019 (1982).

Eckelman and Paik, "Comparison of $^{99m}$Tc and $^{111}$In Labeling of Conjugated Antibodies," *Nuclear Medicinal Biology*, 13(4) 335–343 (1986).

Paik et al., "The Labeling of High Affinity Sites of Antibodies with 99m Tc," *International Journal of Nuclear Medicinal Biology*, 12 (1): 3–8 (1985).

Schwarz et al., "A Novel Approach to Tc–99m Monoclonal Antibodies," *J. Nucl. Med.*, 28: 721 (1987).

Steinstrasser et al., "A Novel Tc–99m Labelled Antibody for in vivo Targeting of Granulocytes," *J. Nucl. Med.*, 29: 925 (1988).

*Primary Examiner*—Jeffrey E. Russel
*Attorney, Agent, or Firm*—Hamilton, Brook, Smith & Reynolds, P.C.

[57] ABSTRACT

A one vial method for labeling a sulfhydryl containing antibody or antibody fragment with technetium-99m is disclosed. The method comprises contacting an antibody mixture comprised of a sulfhydryl containing antibody or antibody fragment and a reducing agent with technetium-99m in an oxidized state. In a preferred embodiment, the antibody mixture further contains a water soluble ligand. A one vial kit for labeling a sulfhydryl containing antibody or antibody fragment with technetium-99m is also disclosed.

8 Claims, 3 Drawing Sheets

U.S. PATENT DOCUMENTS

| | | | |
|---|---|---|---|
| 4,659,839 | 4/1987 | Nicolotti et al. | 548/546 |
| 4,668,503 | 5/1987 | Hnatowich | 530/391.5 |
| 4,671,958 | 6/1987 | Rodwell et al. | 424/1.53 |
| 4,732,974 | 3/1988 | Nicolotti et al. | 530/400 X |
| 4,877,868 | 10/1989 | Reno et al. | 530/389 |
| 5,053,493 | 10/1991 | Pak et al. | 436/547 | ized state. Preferably, the above described antibody
ONE VIAL METHOD FOR LABELING ANTIBODIES WITH TECHNETIUM-99M This is a continuation of application Ser. No. 07/128,328 filed on Dec. 3, 1987, now abandoned.

BACKGROUND OF THE INVENTION

1. Field of the Invention

This invention relates to the field of immunodiagnostics and, more particularly, to methods for labeling antibodies and fragments thereof with metal ions.

2. Background of the Invention

Proteins have been labeled with various radiometals and other radioisotopic elements for use in immunodiagnostic and immunotherapeutic procedures. Some radiometals have superior properties for use in these techniques. Technetium-99m is an ideal radionuclide for scintigraphic imaging because of its nuclear properties. It has a single photon energy of 140 KeV, a half-life of about 6 hours, and it is readily available from a $^{99}$Mo–$^{99m}$Tc generator.

Two general approaches have been taken to label proteins such as antibodies with radiometals. The first is the direct labeling method by which the radiometal is bound to the protein molecule itself. The second is the indirect labeling method in which a chelating agent is coupled to the protein and the radiometal is attached to the protein via the chelating agent.

Rhodes discloses a method of direct labeling of protein with technetium-99m which involves ligand solid phase exchange. See U.S. Pat. No. 4,305,922. According to the method of Rhodes, pertechnetate is reduced to technetium IV and then applied onto a Sephadex® column. The reduced technetium-99m binds to the Sephadex® material. A solution of the protein to be labeled is poured onto the top of the Sephadex column where it is allowed to remain so that ligand exchange occurs. As a result, the technetium-99m is transferred preferentially from the Sephadex material to the protein. The protein may be pretreated with a stannous chloride (a procedure called "pretinning") to enhance transfer of the radiometal to the protein. See U.S. Pat. No. 4,424,200.

Various attempts have been made to label proteins with radiometals by the indirect approach. In one such approach, a chelating agent such as diethylenetriaminepentaacetic acid (DTPA) is conjugated onto the protein and then the metal ion is labeled onto the chelating agent attached to the protein molecule. For example, Khaw et al., *Science* 209: 295–297 (1980) discloses antibodies to cardiac myosin labeled with indium-111 via DTPA and use of the labeled antibodies to image for myocardial infarction. See also, Krejcarek et al., *Biochem. Biophys. Res. Commun.* 77: 581–585 (1977); Childs, R. L. and Hnatowich, D. J., *J. Nucl. Med.* 26: 293 (1985). In a more recent approach, Fritzberg et al. describe the use of particular diamidodithiol and diaminodithiol groups, as a chelating agents. Fritzberg et al, *J. Nucl. Med.* 27: 957 (1986); European Patent Application 86100360.6.

Various degrees of success have been achieved with both the direct and indirect methods of labeling proteins with radiometals. However, the labeled product is often unstable in vivo. Further, techniques for purifying the labeled product before use are often required. A need exists for improved methods for stably labeling proteins for radioimmunodiagnostic and radioimmunotherapeutic procedures.

SUMMARY OF INVENTION

This invention provides a simple, rapid and efficient one vial method for labeling sulfhydryl containing antibodies or antibody fragments with technetium-99m. The method comprises contacting in a single vial an antibody mixture comprised of a sulfhydryl containing antibody or antibody fragment and a reducing agent with technetium-99m in an oxidized state. Preferably, the above described antibody mixture further comprises a water soluble ligand which complexes with reduced technetium-99m. Technetium-99m labeled antibodies or antibody fragment prepared according to the present method are useful for radioimmunodiagnostic purposes such as immunoscintigraphy.

The preferred ligand for use in the method is a polyhydroxydicarboxylic acid or salt thereof having a molecular weight of less than about 10,000 daltons. An especially preferred ligand is D-glucaric acid. D-glucaric acid quickly and stably complexes with technetium-99m in its reduced state and without the formation of significant technetium colloids. When contacted with a sulfhydryl containing antibody, technetium-99m is preferentially transferred to the antibody to form a stable labeled antibody. The preferred metal reducing agents for use in the method are stannous reducing agents such as stannous chloride. These reagents effectively reduce technetium and are pharmacologically acceptable.

The method of this invention can be used to label whole antibodies (e.g., IgG) or antibody fragments (e.g., Fab'). Whole antibodies can be reduced with the reducing agent dithiothreitol (DTT) for example, to produce sulfhydryl containing antibodies. Fab' fragments are especially suited for labeling by the procedure. Under nonoxidizing conditions, these fragments contain free sulfhydryl groups (as they are produced by reduction of disulfide bridges present in F(ab')$_2$ fragments). For most radioimmunodiagnostic techniques, antibody fragments such as Fab' fragments are preferred and thus, the labeling procedure of this invention is particularly suited for preparing radiopharmaceuticals for these techniques.

In the method of the invention, antibody or antibody fragments are radiolabelled with technetium-99m in a simple one vial procedure. For this purpose, kits can be provided with the reagents in a form ready for use on site by the clinician. For example, such a kit can include a single vial containing an antibody mixture comprised of a sulfhydryl containing antibody or antibody fragment, a reducing agent (e.g. stannous ions), and preferably a water soluble ligand (e.g. D-glucaric acid or a salt thereof). The antibody mixture is preferably supplied in lyophilized form although frozen or aqueous forms are also suitable. Technetium-99m (generally in the form of $^{99m}$Tc pertechnetate) is added to the vial and the resulting mixture is incubated for a time sufficient to effect a quantitative transfer of the technetium-99m to the antibody or antibody fragment. The composition can then be injected into the patient without purification. The technetium-99m labeled antibodies and antibody fragments prepared by the method of this invention can be used for diagnostic purposes such as immunoscintigraphy of tumor, myocardial infarction, thromboses, atherosclerotic plaques or bacterial abscess.

The antibody or antibody fragments labeled by the method retain their original immunoreactivity and consequently their target specificity. The radiolabeled antibody is stable in solution and in serum. When Fab' fragments labeled by the method are administered in vivo very little label accumulates in the liver which indicates that the labeled antibody is stable in vivo. In addition, the labeling method can be performed rapidly (it can be completed in less than 15 minutes) and the method can be performed at ambient temperature and at pH 5–9.

It has been found that the ligands employed in preferred embodiments of the present invention are capable of complexing technetium-99m quantitatively in a stable form as a complex without the formation of a significant amount of technetium colloid. Upon contact with a sulfhydryl containing antibody under appropriate conditions, the complexed technetium-99m is transferred substantially quantitatively to sulfhydryl containing antibodies so that radiodiagnostic composition can be prepared with very high specific activity. The labeled product does not require purification before use.

DETAILED DESCRIPTION OF THE INVENTION

Figure 1:
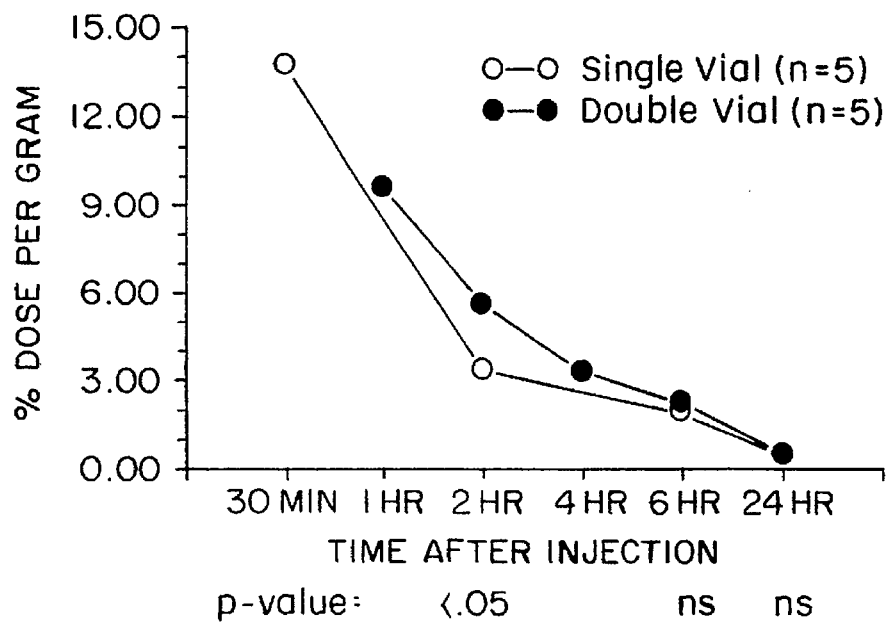
FIG. 1 shows the results of mouse biodistribution studies in blood conducted with antifibrin T2G1S prepared in single vial and double vial labeling kits.

This invention provides a method of radiolabeling protein in a single vial. The reduction of the oxidized form of technetium-99m and the radiolabeling reaction (i.e., the coupling of the radioisotope to protein) are achieved in the same vial. As used herein, the term "vial" refers to any type of reaction vessel and is not intended to be limiting in any way. The method is simple, efficient, and reproducible and it minimizes the safety hazards to persons performing the radiolabeling. The method of this invention is particularly suited for labeling antibodies (polyclonal and monoclonal) for diagnosis. Antibodies can be labeled by this method to a high specific activity with minimal loss of immunoreactivity.

Advantages with the present one vial method over methods using two vials and other known methods for labeling with technetium-99m include: (1) Rapid labeling at ambient conditions. Labeling yields greater than 90% can be achieved in 5–15 minutes at ambient temperature without heating. The clinical advantages of near instantaneous preparation of a diagnostic agent can be substantial. (2) Stability of the lyophilized formulation of the single vial method is superior to the comparable formulation employed in a two vial method. (3) Biodistribution studies of the product resulting from the one vial method show statistically significant differences in key major organs. Uptake in kidney and liver is lower with product produced by this method. Blood clearance is significantly faster. These types of differences would indicate that product from this method would produce lower background, lower absorbed dose to critical organs and faster blood clearance resulting in faster ability to image areas of interest. All these would be substantial clinical advantages. (4) Plasma stability of the product is greater. This provides more viable intact product to serve as the diagnostic agent in vivo.

In a preferred embodiment, an antibody mixture comprised of a sulfhydryl containing antibody or antibody fragment, a reducing agent and a water soluble ligand are added to a vial. Preferably, a sealable reaction vial is used which has means for the introduction and withdrawal of reagent preferably under sterile or semi-sterile conditions. A vial which contains a port for syringe injection is preferred. All reagents can be injected and withdrawn from the reaction vial by syringe, thereby reducing the risk of exposure to radio- or biohazardous reagents. In a most preferred embodiment, the mixture is lyophilized and the vial is presealed and supplied for use in that form. In order to label the antibody or antibody fragment, technetium-99m in an oxidized state is contacted with the antibody mixture. The radiolabeling reaction is then allowed to proceed. The duration and condition of incubation are not critical. Preferably, incubation is conducted for a period from about one minute to about 60 minutes, and most preferably from about 5 minutes to about 30 minutes.

After completion of the labeling reaction, the labeled antibody or antibody fragment is withdrawn from the vial. No separation or purification is required. The entire procedure can be conducted in less than 15 minutes at ambient temperature and at a pH of about 5–9. Under these conditions an essentially complete labeling of the antibody or antibody fragment with technetium-99m can be attained without significant loss of antibody immunoreactivity.

The various reagents used in the method and the parameters of the method are discussed in detail below.

Sulfhydryl Containing Antibodies or Antibody Fragments

The sulfhydryl containing whole antibodies or lower molecular weight antibody fragments can be labeled by the method of this invention. It is believed that sulfhydryl groups constitute at least a part of favored binding sites which exist on molecules and that by the method of this invention, the radiometals either label directly or are preferentially exchanged from the radiometal ligand complex to these favored sites on the molecules. The preferential labeling of these sites on the antibodies molecules results in labeled antibodies of exceptional stability.

Whole antibodies (e.g. IgG) can be provided with sulfhydryl groups by reducing the antibodies with a reducing agent such as dithiothreitol (DTT). Treatment with DTT exposes the sulfhydryl groups by reducing disulfide bridges. For most immunodiagnostic procedures, antibody fragments are preferred reagents. Antibody fragments have a number of advantages over whole antibodies for imaging procedures including, in general, more rapid distribution and accumulation at target site and less immunogenicity. Fab' fragments are monovalent binding antibody which contain free sulfhydryl groups (when maintained under nonoxidizing conditions). Fv fragments could also be prepared to contain free sulfhydryl groups. These fragments can be labelled efficiently by the method of this invention.

Fab' fragments can be prepared from whole antibodies as follows: an antibody molecule is first treated with an endopeptidase such as pepsin to remove the Fc portion of the antibody molecule. The resultant F(ab')₂ fragment is treated with a reducing agent such as DTT or cysteine to reduce disulfide bonds present on the F(ab')₂ fragment resulting in exposed sulfhydryl groups on the molecules and thereby also producing two Fab' molecules for each antibody molecule.

Water Soluble Ligands

In general, the ligands useful in preferred embodiments of the present method are water soluble (or can be made water soluble) chelators which are capable of complexing technetium-99m in the reduced state to form a metal ion/ligand complex. The complex is further capable of exchanging the technetium-99m with a sulfhydryl containing antibody or antibody fragment.

Some of the ligands which can be used in the labeling method of this invention are represented by compounds (including physiologically acceptable salts thereof) having the general formula:

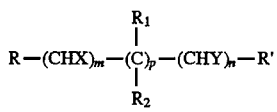

where X and Y are OH or NH₂;

R and R' are independently H, COOH, or CH₂OH or R and R' taken together can form a ring or bi- or multidentate ligand;

m and n are 0–10, such that m+n is at least 2;

R₁ and R₂ are independently H, lower alkyl, substituted lower alkyl, aryl and lower alkylaryl; and p is 0 or 1 provided that, when p is 1, m and n independently are at least 1.

Some of the preferred water soluble ligands for use in the method are presented by the formula:

where R and R' are COOH or CH₂OH, and n=2–10. Among the ligands represented by this formula, polyhydroxydicarboxylic acids having a molecular weight of less than about 10,000 daltons are most preferred. Some specific examples of these types of ligands are D-glucaric acid, glucoheptonic acid, tartaric acid, galactaric acid, arabonic acid, and salts thereof.

The particularly preferred ligand for use in this method is D-glucaric acid. As mentioned, D-glucaric acid complexes with technetium-99m quickly to form a technetium-99m D-glucaric acid complex. Upon contact with a sulfhydryl containing antibody or antibody fragment, substantially quantitative transfer of technetium-99m from the complex to the protein is achieved rapidly and under mild conditions. Although not wishing to be bound by theory, it is believed that the technetium-99m is preferentially transferred to favored binding sites on the protein molecules. This preferential transfer results in a labeled antibody or fragment which is immunoreactive and exceptionally stable in vivo.

Reducing Agents

Reducing agents for use in the method are physiologically acceptable for reducing technetium-99m from its oxidized state to the IV or V oxidization state or for reducing rhenium from its oxidized state. Examples of preferred metal reducing agents which can be used in the method are stannous chloride, stannous fluoride, stannous tartarate, metabisulfite, and sodium dithionite; the most preferred agents are stannous reducing agents especially stannous chloride.

Radioistopes of Technetium

The source of technetium-99m in an oxidized state should preferably be water soluble. Preferred sources are alkali and alkaline earth metal pertechnetate (TcO₄⁻). The technetium-99m is most preferably obtained in the form of fresh sodium pertechnetate from a sterile technetium-99m generator (e.g., from a conventional ⁹⁹Mo/⁹⁹ᵐTc generator). Any other source of physiologically acceptable technetium-99m, however, may be used.

Reaction Conditions

The amount of reducing agent is the amount necessary to reduce the technetium to provide for the binding to the ligand in a reduced state. In a preferred mode, stannous chloride (SnCl₂) is the reducing agent and can range from about 1 to about 1,000 ug/mL preferably about 30 to about 500 ug/mL. The amount of D-glucaric acid (as potassium D-glucarate) can range from about 0.5 mg/mL up to the amount maximally soluble in the medium. Preferred amounts of D-glucaric acid range from about 3 to about 15 mg/mL. The amount of antibody (or fragment) can range from about 0.01 to about 30 mg/mL preferably about 0.17 to about 1.5 mg/mL. Finally, technetium-99m in the form of pertechnetate can be in amounts used up to about 500 mCi/mL preferably about 1 to about 50 mCi/mL. The amount of mCi per mg of antibody is preferably about 3 to about 150.

The reaction between the above described antibody mixture and the metal ion is preferably carried out in an aqueous solution at a pH at which the protein is stable. By "stable", it is meant that the protein remains soluble and retains its biological activity. Normally, the pH for the reaction will be a pH from about 5 to about 9, the preferred pH being about 6 to about 8. The metal ion transfer chelate complex and the antibody are incubated, preferably at a temperature from about 20° C. to about 60° C., most preferably from about 20° C. to about 37° C., for a sufficient amount of time to allow for complexation of the metal ion with the antibody. Generally, less than 30 minutes are sufficient to complete the transfer reaction under these conditions. Times of five to fifteen minutes are routinely achievable.

Kits for Performing the Method

The reagents for performing the present labeling method are assembled in single vial kit for convenient performance in the clinic. In one embodiment, the kit contains one vial (sealed and sterile) containing a sulfhydryl containing antibody or antibody fragment, a reducing agent (preferably stannous ions) and a water soluble ligand (preferably D-glucaric acid or a salt thereof). These kits can be used when technetium-99m is provided by the user. The kits are designed to contain the appropriate antibody or antibody fragment(s) for any particular immunodiagnostic or immunotherapeutic procedure (some of which are discussed below).

The reagents in the kit can be provided in aqueous, frozen or lyophilized form. Lyophilized preparations can be diluted with aqueous medium upon use. The amount of reagents in each vial can vary according to the chosen parameters of the method (see above under Reaction Conditions). The labeling procedure can be performed simply by adding technetium-99m (for example, in the form of aqueous sodium pertechnetate) to the vial containing the antibody or antibody fragment, reducing agent and, in a preferred embodiment, water soluble ligand. The contents of the vial are then mixed and incubated for a time sufficient to effect labeling of the antibody or antibody fragment. The radiolabeled antibody or antibody fragment can then be used immediately without purification.

Use of the Labeled Antibodies in Immunodiagnostics

Technetium-99m labeled antibodies or antibody fragments can be used in immunoscintigraphy. One important use is in the imaging of tumors. As mentioned, antibody fragments are preferred for most immunoscintigraphic techniques. Labeled Fab' fragments of tumor specific antibodies can be prepared and used to image primary or secondary tumors. In general, the technetium-99m labeled antibody fragment is prepared by combining an aqueous antibody mixture of an Fab' fragment specific for the tumor, a reducing agent, and a water soluble ligand with $^{99m}Tc$ (usually in the form of pertechnetate).

The labeled Fab' fragment can then be injected parenterally (preferably intravenously) into a subject. After injection, sufficient time is allowed for the labeled Fab' fragment to accumulate at the site of the tumor. The subject is then scanned with a gamma camera to detect the gamma emission of the technetium-99m and to thereby obtain an image of the tumor. In this way the tumor can be localized and its size can be determined.

Tumor specific antibody fragments for use in these procedures can be derived from anticolorectal cancer antibody, antilung cancer antibody, antiovarian cancer antibody, antibreast cancer antibody, and antiprostate cancer antibody. Some specific examples of tumor specific antibodies which can be labeled by the method of this invention and used to image tumors are the monoclonal antibodies 17-1A and 19-9 (gastrointestinal), CA 125 (ovarian) and 103D2 (breast).

Antibodies labeled by the method of this invention can be used to label myocardial infarcts. The imaging of myocardial infarcts to determine their size and location is described by Haber, U.S. Pat. No. 4,421,735, the disclosure of which is incorporated herein by reference. In brief, employing the labelling method of this invention, an image of a myocardial infarct in a subject can be obtained by first preparing a $^{99m}Tc$ labeled myosin specific Fab' fragment by combining an aqueous mixture of a myosin specific Fab' fragment, a metal reducing agent and, preferably, a water soluble ligand with $^{99m}Tc$. The labeled myosin specific fragment is then intraveneously injected into a subject (for example, after coronary occlusion). The labeled fragment is allowed to localize at the site of the infarct and an image of the infarct is obtained by scanning the area of the heart with a gamma camera. A preferred antibody for production of labeled myosin specific Fab' fragments is the monoclonal antibody R11D10.

In addition, fibrin specific Fab' fragments can be labelled by the procedure of this invention to provide reagents for imaging blood clots. A $^{99m}Tc$ labeled fibrin specific fragment is prepared by combining an aqueous antibody mixture of a fibrin specific Fab' fragment, a metal reducing agent and, preferably, a water soluble ligand with $^{99m}Tc$. The $^{99m}Tc$ labeled fibrin specific fragment is injected into the subject. After allowing the fragment to localize at the site of the blood clot, the subject is scanned to obtain an image of the clot. Fibrin specific antibodies which are not cross reactive with fibrinogen are the preferred antibodies for this imaging technique. A preferred antibody for production of labeled fibrin specific Fab' fragments is the monoclonal antibody T2G1s.

Antibody fragments specific for bacteria can be used in immunoscintigraphic techniques for obtaining an image of a bacterial abscess in a subject. For this purpose, anti-bacterial or anti-macrophage antibody fragments are employed. Antibodies against a commont determinant of gram-negative bacteria (e.g., anti-lipid A antibody) can be used to image an abscess caused by a gram-negative micro-organism. The antibody is labeled with technetium-99m as described above injected into the subject and allowed to localize at the abscess. The subject is then scanned with the photoscanning equipment to obtain an image of the abscess.

The invention is further defined by the following example wherein all parts and percentages are by weight and degrees are Celsius unless otherwise stated.

EXAMPLE AND COMPARATIVE EXPERIMENTS

A. Example 1: One Vial Method

1. Preparation of the T2G1s Fab' Antibody Fragment

T2G1s F(ab')$_2$ antibody fragment (162 mg) in tris buffer (15.5 ml, 0.05M, pH 8.0) with sodium chloride (0.1M) was treated with DTT (1 mM) for 1–2 hours at ambient temperature. The resulting mixture was purified by diafiltration under argon by exchange with 20 volumes of sodium phosphate buffer (0.05M, pH 6.4) containing sodium chloride (0.1M) and EDTA (0.001M) to yield a solution containing T2G1s Fab' (135 mg, concentration 1 mg/mL).

2. Preparation of a Single Vial Kit for Technetium-99m Labeling of T2G1s Antifibrin Antibody Fab' Fragment To a degassed solution (5 mL) of monopotassium D-glucaric acid (12.5 mg/mL, 0.05M) in potassium phosphate buffer (0.05M, pH 6.4) with EDTA (0.0005M), and sodium chloride (0.16M) was added stannous chloride solution (7.5 uL, 0.1 mg/mL in 1N HCl). To this solution (4.7 mL) was added a solution of murine monoclonal antibody Fab' fragment derived from cell line T2G1s (0.312 mL, 8 mg/mL in 0.05M potassium phosphate buffer pH 6.4 containing 0.1M sodium chloride and 0.001M EDTA) prepared as described in subsection A.1 above. After thorough mixing, portions (1.0 mL) were dispensed into serum vials, lyophilized then sealed with a rubber vial closure.

3. Radiolabeling the Antibody Fab' Fragment with Technetium-99m in a Single Vial Kit In a one vial procedure sodium ($^{99m}Tc$) pertechnetate (1.0 mL, 20 mCi) was added to the vial of T2G1s Fab' described in subsection A.2 above. The solution was allowed to stand at ambient temperature and the mixture was analyzed at intervals using chromatography on Whatman™ 3MM paper eluting with acetonitrile:water (7:3). In this system, product remained at the origin while ($^{99m}$Tc) pertechnetate and reduced complexed technetium-99m migrated off the origin. Completeness of reaction was determined by the percent of radiolabeled product at the origin. Further dilutions were made, if required, using saline (0.9%). The product of this one vial method was further analyzed as described in Section C below.

B. Comparative Experiments: Two Vial Methods

1. Preparation of a Two Vial Kit for Technetium-99m Labeling of T2G1s Antifibrin Antibody Fab' Fragment a) Solution Formulation of the Antibody Fragment A vial was prepared to contain T2G1s Fab' (0.5 mg), prepared substantially as described above in subsection A.1 above, in a buffer solution (1.0 mL) of potassium phosphate (0.05M, pH 6.4), sodium chloride (0.1M) and EDTA (0.001M). The vial was sealed with a rubber vial closure.

b) Lyophilized Formulation of the Antibody Fragment

A vial was prepared to contain T2G1s Fab' (0.5 mg), prepared substantially as described above in subsection A.1 above, in a buffer solution (1.0 mL) of potassium phosphate (0.05M, pH 6.4), sodium chloride (0.05M), lactose (0.05M) and EDTA (0.0005M). The contents of the vial were lyophilized and then sealed with a rubber vial closure.

2. Preparation of the Stannous Composition for the Two Vial Method

Using anaerobic conditions, vials were prepared to contain a solution (1.0 ml) of monopotassium D-glucaric acid (12.5 mg, 0.05 mmol), stannous chloride (150 ug, 0.79 umol) and sodium bicarbonate (16.8 mg, 0.2 mmol, pH 7.6). The contents of vial were lyophilized and then sealed with a rubber vial closure.

3. Radiolabeling the Antibody Fab' Fragment with Technetium-99m in Two Vial Kit In the two vial procedures sodium ($^{99m}$Tc) pertechnetate (1.0 mL, 20 mCi) was added to the stannous composition described above. After 10 minutes 0.5 mL of this solution was added to the solution and lyophilized formulations of the T2G1s Fab' described in subsections a) and b) above. The product was analyzed as described in Section C.

C. Comparison of Labeled T2G1s Antifibrin Antibody Fab' Fragments

1. Determination of the Immunoreactivity of the Technetium-99m Labeled T2G1s Fab'

Immunoreactivity of the labeled antibody was tested by applying an aliquot of the antibody reaction mixtures to an affinity column (the first seven amino acids of the amino terminus of the beta chain of human fibrin, coupled to CNBr-Sepharose 6B). The volume of the packed bed was 1 mL. The column was eluted with 10 mL of 1% BSA in 0.01M sodium phosphate, 0.145M NaCl, pH 7.0, followed by elution with 10 mL of 0.1M glycine, pH 2.5. During these elutions, 1 milliliter fractions were collected and counted in a NaI(T1) well counter. The percent immunoreactivity was computed as:

$$\% \text{ immunoreactivity} = \frac{\text{total net counts eluted by glycine}}{\text{total net counts eluted by both solutions}} \times 100$$

The results are shown in Tables 1 and 2.

2. Comparison of Labeling Rates of the One Vial and Two Vial Kits

Table 1 also shows rates of labeling for the one vial and two vial kits as determined by % protein incorporation according to the paper chromatography technique described in subsection A.3 above. The results show that the one vial kit produces labeled product faster than the two vial kits.

TABLE 1

Labeling Ratio of One Vial and Two Vial Kits

| Kit | Storage Temp (°C.) | Age When Tested (Days) | % Protein Incorporation | | | | Immunoreactivity (%) |
|---|---|---|---|---|---|---|---|
| | | | 5' | 15' | 30' | 60' | |
| Two Vial Solution | 4° | 7 | NA | 65 | 78 | 87 | 78 |
| Two Vial Lyophilized | 4° | 7 | 61 | 86 | 89 | 93 | 93 |
| One Vial | 4° | 6 | 93 | 94 | 95 | 95 | 98 |

3. Comparison of the Stability of the One Vial and Two Vial Kits

The stability of the one vial and two vial kits were determined by % protein incorporation according to the paper chromatography described in subsection A.3 above at both 4° and 37°. The results are shown in Table 2. The results demonstrate that the one vial kit maintains superior labeling efficiency in the 12–17 day period when stored at 37°.

TABLE 2

Stability of One Vial and Two Vial Kits

| Kit | Storage Temp (°C.) | Age When Tested (Days) | % Protein Incorporation | | | | Immunoreactivity (%) |
|---|---|---|---|---|---|---|---|
| | | | 5' | 15' | 30' | 60' | |
| Two Vial Solution | 4° | 14 | NA | 75 | 84 | 92 | 82 |
| | 37° | 14 | NA | 35 | 45 | 59 | 40 |
| Two Vial Lyophilized | 4° | 17 | 91 | 85 | 94 | 96 | 98 |
| | 37° | 17 | 52 | 80 | 92 | 96 | 98 |
| One Vial | 37° | 12 | 87 | 96 | 97 | 98 | 96 |

Biodistribution in Mice

Figure 2:
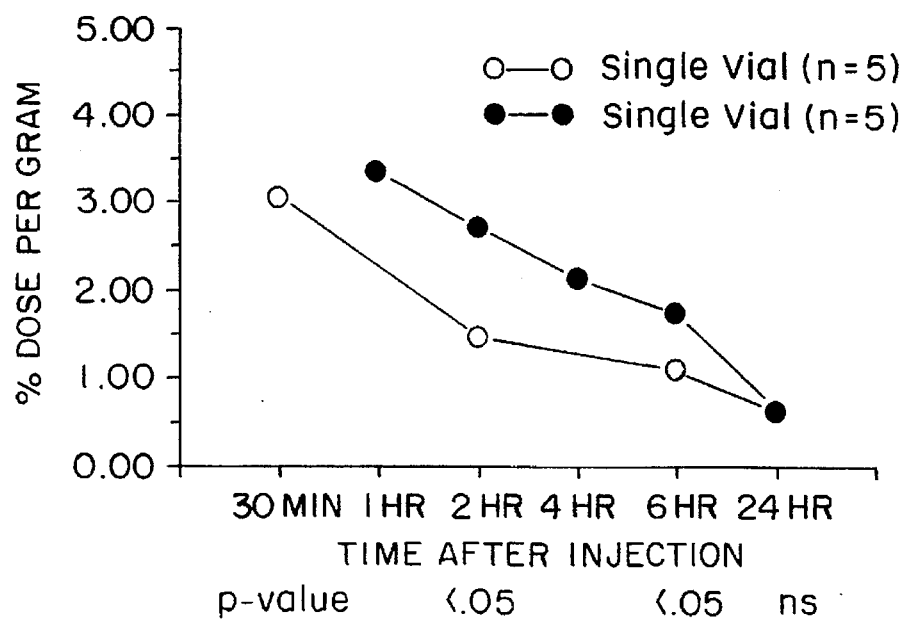
FIG. 2 shows the results of mouse biodistribution studies in liver conducted with antifibrin T2G1S prepared in single vial and double vial labeling kits.
Figure 3:
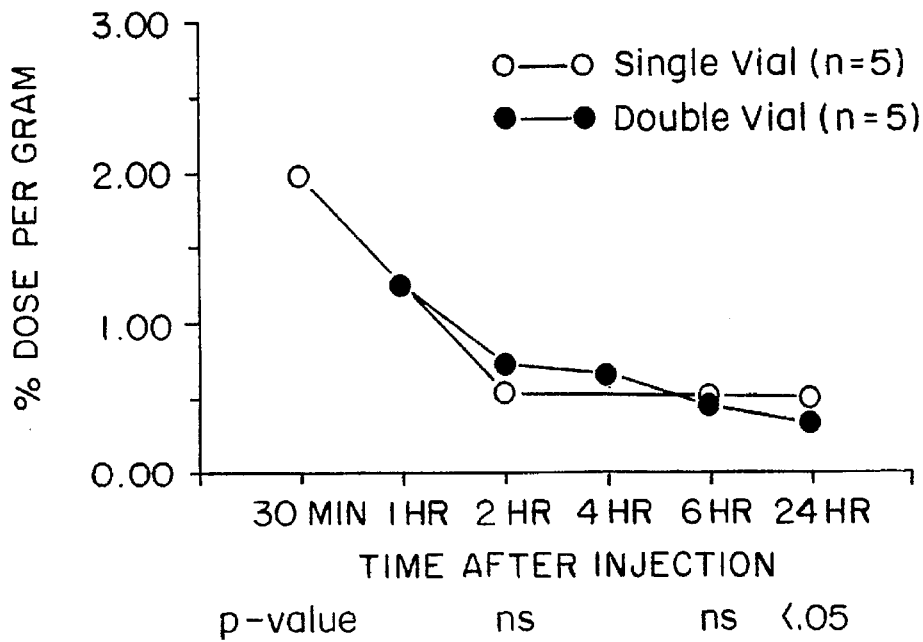
FIG. 3 shows the results of mouse biodistribution studies in spleen conducted with antifibrin T2G1S prepared in single vial and double vial labeling kits.
Figure 4:
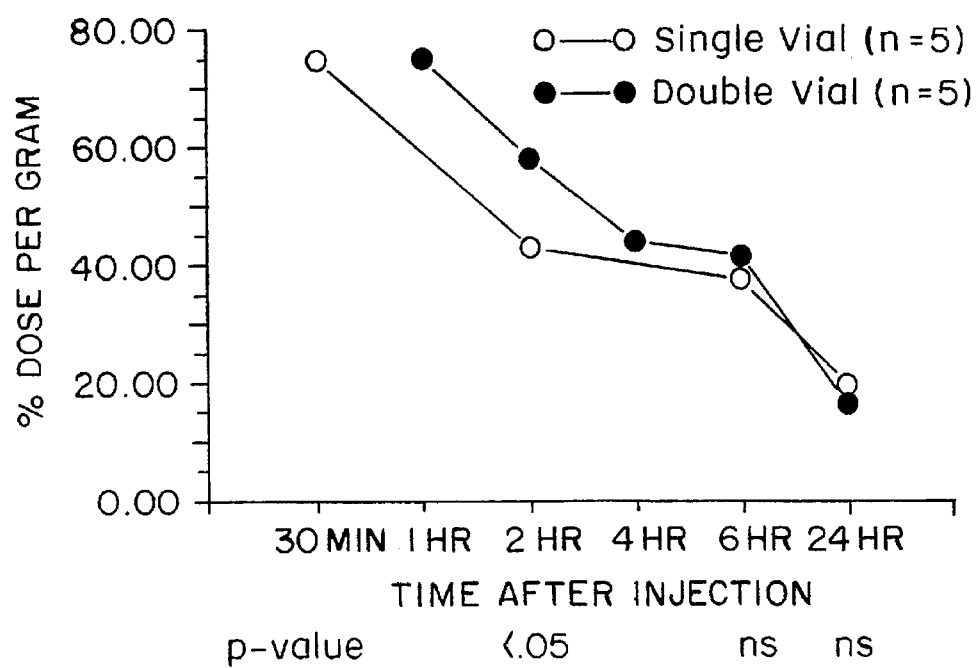
FIG. 4 shows the results of mouse biodistribution studies in kidney conducted with antifibrin T2G1S prepared in single vial and double vial labeling kits.
Figure 5:
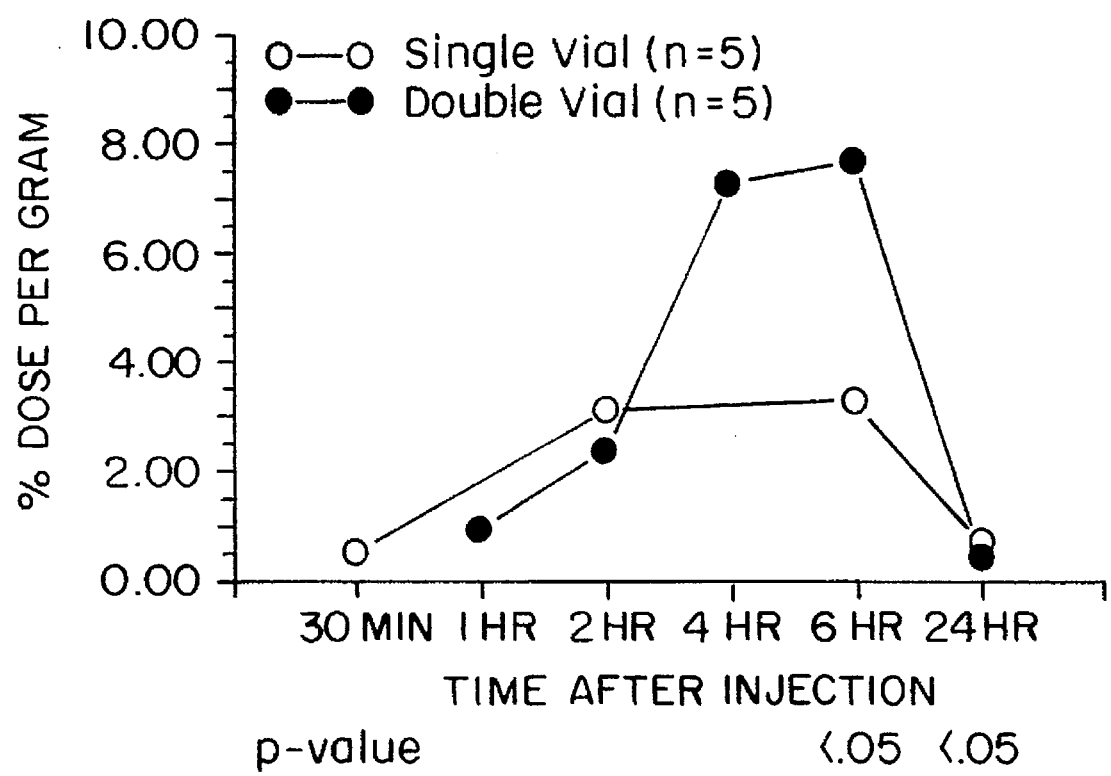
FIG. 5 shows the results of mouse biodistribution studies in large intestine conducted with antifibrin T2G1S prepared in single vial and double vial labeling kits.

Mouse biodistribution of labeled antibody fragments prepared according to the one vial kit and two vial solution kit described above in Sections A and B was examined by injecting mice I.V. with the labeled fragments and determining the relative amounts of radiolabel accumulated in different tissues. The results are shown in Table 3 and FIGS. 1–5. The results show statistically significant differences favoring the one vial kit in every organ system evaluated.

TABLE 3

ANTIFIBRIN T2G1S MOUSE BIODISTRIBUTION STUDY COMPARISON OF SINGLE VIAL AND DOUBLE VIAL PREPARATIONS MEAN PERCENT DOSE PER GRAM IN FIVE ANIMALS

| Organ System | Time After Injection (Hours) | Single Vial (Mean +/− SD) | Double Vial (Mean +/− SD) | p-value |
|---|---|---|---|---|
| Blood | 2.0 | 3.39 ± 0.17 | 5.64 ± 0.53 | <0.05 |
| | 6.0 | 1.88 ± 0.25 | 2.21 ± 0.28 | ns |
| | 24.0 | 0.48 ± 0.07 | 0.52 ± 0.08 | ns |
| Heart | 2.0 | 0.90 ± 0.11 | 1.34 ± 0.23 | <0.05 |
| | 6.0 | 0.56 ± 0.06 | 0.58 ± 0.23 | ns |
| | 24.0 | 0.45 ± 0.04 | 0.25 ± 0.03 | <0.05 |
| Lungs | 2.0 | 1.36 ± 0.23 | 3.17 ± 0.31 | <0.05 |
| | 6.0 | 0.88 ± 0.14 | 1.49 ± 0.42 | <0.05 |
| | 24.0 | 0.41 ± 0.05 | 0.44 ± 0.06 | ns |
| Liver | 2.0 | 1.48 ± 0.17 | 2.73 ± 0.41 | <0.05 |
| | 6.0 | 1.11 ± 0.16 | 1.75 ± 0.23 | <0.05 |
| | 24.0 | 0.64 ± 0.03 | 0.65 ± 0.07 | ns |
| Spleen | 2.0 | 0.54 ± 0.15 | 0.73 ± 0.09 | ns |
| | 6.0 | 0.51 ± 0.12 | 0.45 ± 0.15 | ns |
| | 24.0 | 0.51 ± 0.09 | 0.33 ± 0.02 | <0.05 |
| Kidneys | 2.0 | 42.98 ± 7.65 | 58.00 ± 6.63 | <0.05 |
| | 6.0 | 37.70 ± 6.54 | 41.59 ± 9.13 | ns |
| | 24.0 | 19.85 ± 1.83 | 16.60 ± 2.90 | ns |
| Stomach | 2.0 | 0.34 ± 0.07 | 0.94 ± 0.31 | <0.05 |
| | 6.0 | 0.85 ± 0.83 | 1.05 ± 0.52 | ns |
| | 24.0 | 0.35 ± 0.10 | 0.29 ± 0.12 | ns |
| Small Intestine | 2.0 | 1.40 ± 0.44 | 3.63 ± 0.84 | <0.05 |
| | 6.0 | 0.75 ± 0.22 | 1.38 ± 0.34 | <0.05 |
| | 24.0 | 0.28 ± 0.04 | 0.24 ± 0.05 | ns |
| Large Intestine | 2.0 | 3.13 ± 0.33 | 2.39 ± 0.89 | ns |
| | 6.0 | 3.30 ± 1.31 | 7.67 ± 1.96 | <0.05 |
| | 24.0 | 0.73 ± 0.19 | 0.40 ± 0.11 | <0.05 |
| Muscle | 2.0 | 0.19 ± 0.03 | 0.46 ± 0.20 | <0.05 |
| | 6.0 | 0.15 ± 0.06 | 0.18 ± 0.03 | ns |
| | 24.0 | 0.29 ± 0.03 | 0.11 ± 0.03 | <0.05 |
| Gonads | 2.0 | 0.36 ± 0.09 | 1.35 ± 0.39 | <0.05 |
| | 6.0 | 0.29 ± 0.07 | 0.64 ± 0.14 | <0.05 |
| | 24.0 | 0.33 ± 0.06 | 0.18 ± 0.03 | <0.05 |

4. Comparison of Plasma Stability of the One Vial and Two Vial Kits

Labeled antibody was prepared as described in the above examples and comparative experiment (solution formulation). The $^{99m}$Tc labeled T2G1s Fab' fragments (100 uL) were added to citrated plasma (50 uL). Table 4 compares the plasma stability as determined by % protein incorporation at 37° of the products from the one vial and two vial kits versus control (no plasma added). The results show that the plasma stability of the one vial kit is better than the two vial kit.

TABLE 4

Plasma Stability of One Vial and Two Vial Kits

| Kit | No Plasma Added (Control) % Incorporation | | | | Plasma Added % Incorporation | | | |
|---|---|---|---|---|---|---|---|---|
| | 15' | 3 hr | 6 hr | 24 hr | 1 hr | 2 hr | 6 hr | 24 hr |
| Two Vial Solution | 92 | 69 | 90 | 78 | 88 | 78 | 73 | 69 |
| One Vial | 88 | 90 | 84 | 89 | 90 | 88 | 86 | 83 |

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A one vial method for labeling a free-sulfhydryl-containing antibody or antigen-binding fragment thereof with technetium-99m with a labeling yield exceeding 90%, comprising:

a. providing a vial containing a solution of an antibody mixture comprised of;
      i. a free sulfhydryl containing antibody or antigen-binding fragment thereof;
      ii. an agent for reducing technetium; and
      iii. a D-glucaric acid or a salt there of; and
   b. adding to the vial a solution of technetium-99m in an oxidized state.

2. A method according to claim 1, wherein the sulfhydryl containing antibody is reduced IgG.

3. A method according to claim 1, wherein the antigen-binding fragment is a Fab' fragment.

4. A method according to claim 3, wherein Fab' is produced by reducing an F(ab')$_2$ with DTT.

5. A method according to claim 1, wherein the reducing agent is a stannous reducing agent.

6. A method according to claim 1, wherein the antibody mixture is lyophilized.

7. A method according to claim 1, wherein the technetium-99m is added as an aqueous solution of sodium ($^{99m}$Tc) pertechnetate.

8. A method for labeling a Fab' antibody fragment with technetium-99m with a labeling yield exceeding 90% comprising:

a. providing a vial containing a lyophilized mixture of:
      i. an Fab' antibody fragment;
      ii. a stannous reducing agent; and
      iii. D-glucaric acid; and
   b. adding to the vial an aqueous solution of sodium ($^{99m}$Tc) pertechnetate.

* * * * *